(12) United States Patent
Wang (10) Patent No.: US 11,033,297 B2
(45) Date of Patent: Jun. 15, 2021

(54) PARACENTESIS NEEDLE FRAME

(71) Applicant: Qin Wang, Jiangsu (CN)

(72) Inventor: Qin Wang, Jiangsu (CN)

( * ) Notice: Subject to any disclaimer, the term of this patent is extended or adjusted under 35 U.S.C. 154(b) by 404 days.

(21) Appl. No.: 15/773,930

(22) PCT Filed: Dec. 25, 2015

(86) PCT No.: PCT/CN2015/099034
§ 371 (c)(1),
(2) Date: May 4, 2018

(87) PCT Pub. No.: WO2017/075882
PCT Pub. Date: May 11, 2017

(65) Prior Publication Data
US 2019/0069923 A1   Mar. 7, 2019

(30) Foreign Application Priority Data

Nov. 8, 2015  (CN) .......................... 201510752954.2
Nov. 8, 2015  (CN) .......................... 201510753024.9
Dec. 18, 2015 (CN) .......................... 201510957857.7

(51) Int. Cl.
*A61B 17/34*   (2006.01)
*A61B 8/08*    (2006.01)
(Continued)

(52) U.S. Cl.
CPC ........ *A61B 17/3403* (2013.01); *A61B 8/0841* (2013.01); *A61B 17/34* (2013.01);
(Continued)

(58) Field of Classification Search
CPC ........ A61B 17/3403; A61B 2017/3409; A61B 2017/3405; A61B 90/11; A61B 90/10;
(Continued)

(56) References Cited

U.S. PATENT DOCUMENTS 4,877,033 A    10/1989   Seitz, Jr.
6,361,499 B1 *  3/2002   Bates .................. A61B 8/0833
                                                  600/461
(Continued)

FOREIGN PATENT DOCUMENTS

CN    2885145 Y    4/2007
CN    2915028 Y    6/2007
(Continued)

OTHER PUBLICATIONS

International Search Report for PCT/CN2015/099034, dated Aug. 8, 2016, 3 pages.

*Primary Examiner* — Angela M Hoffa
*Assistant Examiner* — Amal Aly Farag
(74) *Attorney, Agent, or Firm* — Blank Rome LLP (57) ABSTRACT

A needle guide holder, which is used for a fixing medical puncture needle and a ultrasonic probe, comprises a holder body (1a, 1b) and a fixing device (2a, 2b) used in cooperation with the holder body (1a, 1b). The fixing device (2a, 2b) is mounted onto the holder body (1a, 1b) and provided with a weakening portion (23a, 23b). The needle guide holder is designed to be disposable, thereby avoiding the possibility of cross-infection caused by using the same needle guide holder on different patients. The needle guide holder can be used on one and same patient to perform a number of treatments just through the replacement of a sliding frame and without replacing the fixing device and a fixing frame. In a treatment process, the puncture needle is left in the body for a subsequent treatment, while the needle guide holder and the ultrasonic probe can be removed from the human body.

10 Claims, 10 Drawing Sheets

(51) Int. Cl.
*A61B 90/00* (2016.01)
*A61B 17/00* (2006.01)

(52) U.S. Cl.
CPC ... *A61B 17/3401* (2013.01); *A61B 2017/0023* (2013.01); *A61B 2017/3405* (2013.01); *A61B 2017/3413* (2013.01); *A61B 2090/0814* (2016.02)

(58) Field of Classification Search
CPC .............. A61B 17/34; A61B 8/0841; A61B 2090/0814; A61B 2017/3413; A61B 17/3401; A61B 2017/0023
USPC .................................................. 600/461, 464
See application file for complete search history.

(56) References Cited

U.S. PATENT DOCUMENTS

| | | |
|---|---|---|
| 6,758,817 B1 | 7/2004 | Pruter et al. |
| 2005/0059891 A1* | 3/2005 | Kosaku .............. A61B 17/3403 600/439 |
| 2009/0143684 A1* | 6/2009 | Cermak .............. A61B 8/4422 600/461 |
| 2010/0168766 A1* | 7/2010 | Zeng .................. A61B 17/3403 606/130 |
| 2011/0028847 A1* | 2/2011 | Whitmore, III ....... A61B 90/11 600/461 |
| 2012/0016316 A1 | 1/2012 | Zhuang et al. |
| 2013/0144193 A1 | 6/2013 | Lewis, Jr. et al. |
| 2019/0282262 A1* | 9/2019 | Bouazza-Marouf ........................ A61B 17/3403 |

FOREIGN PATENT DOCUMENTS

| | | |
|---|---|---|
| CN | 101983620 A | 3/2011 |
| CN | 103140173 A | 6/2013 |
| CN | 203263506 U | 11/2013 |
| CN | 203263507 U | 11/2013 |
| CN | 104173107 A | 12/2014 |

* cited by examiner

PARACENTESIS NEEDLE FRAME

RELATED APPLICATIONS

This application is a national phase of PCT/CN2015/099034, filed on Dec. 25, 2015, which claims the benefit of Chinese Application No. 201510752954.2, tiled on Nov. 8, 2015, Chinese Application No. 201510753024.9, filed on Nov. 8, 2015 and Chinese Application No. 201510957857.7, filed on Dec. 18, 2015. The entire contents of those applications are hereby incorporated by reference.

TECHNICAL FIELD

The present invention relates to the technical field of interventional ultrasonic tools, in particular to a needle guide holder.

BACKGROUND ART

In the medical needle guide field, many needle guide holders are made of medical stainless steel materials, and all of them are reusable needle guide holders, which brings such a problem such as the guides must be sterilized before each use. These reused needle guide holders may result in cross-infection among different patients due to incomplete disinfection, thereby affecting the health of the patients and even causing medical accidents. In densely populated countries, due to a large number of patients and a small number of reusable needle guide holders, there are frequent occurs of insufficient disinfection time and incomplete disinfection.

The Chinese patent "Intracavitary Probe and Needle guide", with a patent number of CN 101983620B, discloses the following contents: "comprising a needle guide seat and a gland buckled on the needle guide seat, wherein the needle guide seat is opened, at the top thereof, with an elongated semi-circular groove, and the elongated semi-circular groove and a lower surface of the gland, together, form an elongated guide hole capable of receiving and guiding a puncture needle; the gland is provided, at a front portion thereof, with a forwardly protruding flange for the insertion of probe housing. At a rear portion of the gland, an elastically protruding edge for holding the probe housing tightly is provided, and the elastically protruding edge has a positioning rib; the needle guide seat is also provided, at a rear portion thereof, a second convex rib for positioning with the probe housing; the gland is provided with an inner bent edge for holding the needle guide seat tightly, and the needle guide seat is provided with a snap groove in coordination with the inner bent edge; and the gland is provided with a first groove for locking the needle guide seat, and the needle guide seat is provided with a first convex rib in coordination with the first groove". The technical solution of this patent, which still solves the problems of a repeated use and a convenient disassembly of the needle guide and related components, cannot guarantee a one-time use of the needle guide and still has the possibility of cross-infection caused by using the same set of needle guide on different patients.

The selections of many needle guide holder puncture holes are mostly achieved through the replacement with different needle guide holders, and each needle guide holder can only fit one puncture needle. In this case, different needle guide holders need to be provided for different puncture needles, thereby largely reducing the adaptability of the needle guide holder and increasing the cost. The needle guide holders in the prior art mostly adapt to the difference in the depth of the check site by an angle change regulation device, but are deficient in the application of puncture needles with different diameters.

The Chinese patent "Needle guide", with a patent number of CN203263506U, discloses the following contents: "comprising: a mounting seat detachably mounted on an ultrasonic probe, a mounting plate extending from the mounting seat; and an angle support detachably mounted on the mounting plate, the angle support being formed with a guide hole for receiving and guiding a puncture needle, wherein the needle guide makes the angle support rotatable relative to the mounting plate, by the coordination between one positioning structure and at least two positioning points respectively provided on the mounting plate and the angle support, to provide options of different puncture angles, and, meanwhile, can ensure that each puncture needle guide line is close to the probe so as to minimize the blind zone". This patent solves the technical problem of making the puncture angle adjustable, but cannot meet the requirement of being suitable for puncture needles of different specifications and sizes.

Moreover, the current traditional needle guides cannot accurately adjust the needle insertion angle.

SUMMARY OF THE INVENTION

In order to overcome the following technical defects: conventional needle guide holders in the prior art cannot be guaranteed a single use so that there exists the possibility of cross-infection caused by using the same needle guide holder by different patients, cannot be used with puncture needles of different specifications and sizes, and cannot accurately adjust the needle insertion angle, the present invention provides a needle guide holder, which can guarantee a single use of the needle guide holder, make the needle guide to adapt to different puncture needles on the same ultrasonic probe, and at the same time conveniently and accurately adjust the needle insertion angle.

In order to achieve the above purposes, the present invention adopts the following technical solution:

A needle guide holder for fixing a medical puncture needle and a ultrasonic probe, comprising: a holder body and a fixing device used in cooperation with the holder body, the fixing device being mounted onto the holder body and provided with a weakening portion.

The fixing device of the needle guide holder is mounted onto the holder body, and the holder body of the needle guide holder cannot be detached from the fixing device. Meanwhile, the fixing device is provided with a weakening portion. The user can destroy the fixing device through the weakening portion so that the entire needle guide holder is destroyed and cannot be reused, thereby achieving the purpose of a single use of the needle guide holder and avoiding the possibility of cross-infection caused by using the same needle guide holder by different patients.

Preferably, the holder body comprises a fixing frame and a sliding frame detachably mounted to the fixing frame, and a puncture needle groove is provided on the sliding frame. When there is a need to replace the puncture needle, it is only required to detach and replace the sliding frame so as to adapt to puncture needles of different diameters, thus examine different sites. In this case, there is no need to replace the entire needle guide holder, thereby saving the cost and replacement time of the needle guide holder. Meanwhile, in a treatment process, the fixing frame can be separated from the sliding frame so as to realize a function that the puncture needle is left in the human body for a subsequent treatment, while the needle guide holder and the ultrasonic probe can be removed from the human body.

Preferably, the sliding frame has a sliding portion and a snapping portion, both sides of the sliding portion each being provided with a protrusion, and the puncture needle groove being provided at a bottom of the sliding portion; and both sides of the snapping portion are each provided with an elastic snap lock, each elastic snap lock having a projection thereon. The fixing frame is provided with a sliding groove at each location thereon that in cooperation with the protrusion, the fixing frame being slidable in the sliding groove. The fixing frame is provided with an accommodating groove at each location thereon that corresponds to the elastic snap lock, the elastic snap lock being slidable in the accommodating groove; and the accommodating groove is provided with a snap groove at each location therein that corresponds to the projection, the projection being placeable in the snap groove.

Preferably, both sides of the fixing frame are each provided with a through groove, each through groove having a first boss therein. The fixing device comprises a pull strip and snap strips connected to the pull strip at both sides of an end of the pull strip, respectively, both of the snap strips each being connected to the pull strip via the weakening portion. Each of the snap strips is provided with at least one barb-like buckle in cooperation with the through groove, the barb-like buckle being provided with a second boss at each location thereon that corresponds to the first boss, wherein the holder body and the fixing device are fixedly connected by means of snap connection of the first bosses and the second bosses.

After the needle guide holder has been used, the fixing device is pulled off from the position of the weakening portion by pulling the pull strip so as to separate the pull strip from the snap strips, thereby realizing a pull-off self-destructive design of the needle guide holder, so that the possibility of cross-infection caused by using the same needle guide holder by different patients can be avoided.

Preferably, the weakening portion is a row of discontinuous through holes or a groove.

Further, the holder body comprises a fixing frame and a rotary needle holder assembly, the fixing frame being rotatably connected to the rotary needle holder assembly.

The fixing frame is rotatably connected to the rotary needle holder assembly so that the needle insertion angle can be adjusted conveniently and accurately.

Further, the rotary needle holder assembly comprises a rotary needle holder body and a sliding frame detachably mounted to the rotary needle holder body, wherein the sliding frame is provided with a puncture needle groove thereon.

When it is required to replace the puncture needle, it is only required to detach and replace the sliding frame so as to adapt to puncture needles of different diameters, thus examining different sites. In this case, there is no need to replace the entire needle guide holder, thereby saving the cost and replacement time of the needle guide holder. Meanwhile, in a treatment process, the rotary needle holder body can be separated from the sliding frame so as to realize a function that the puncture needle is left in the human body for a subsequent treatment, while the needle guide holder and the ultrasonic probe can be removed from the human body.

Further, both sides of the sliding frame are each provided with a guide rail, each guide rail being provided with a snap bump. The rotary needle holder body is provided with a guide groove at each location thereon that corresponds to the guide rail, the guide groove being provided with a snap pit at each location thereon that corresponds to the snap bump, wherein the snap bump can be placeable in the snap pit, and the guide rail is slidable in the guide groove.

Furthermore, the fixing frame has a connecting portion at its right end, the connecting portion being provided with a pair of rotation holes, two pairs of angle adjusting holes and a pair of arc-shaped holes therein, wherein the angle adjusting holes and the arc-shaped holes are all located on arcs of circles formed with the rotation holes being centers of the circles, and a plane where the circles lie is perpendicular to a straight line where the pair of rotation holes are located. The rotary needle holder body is provided with a columnar protrusion at each location thereon that corresponds to the rotation holes, with an angle adjusting bump at each location thereon that corresponds to the angle adjusting holes, and with a circular hole at each location thereon that corresponds to the arc-shaped holes, wherein the columnar protrusions are all placeable in the rotation holes; the angle adjusting bumps are placeable in the angle adjusting holes; and the rotary needle holder assembly is further provided with two buttons, the buttons each being provided, in the middle thereof, with a snap groove, each snap groove being placed in the arc-shaped holes and the circular holes.

Further, the materials of the holder body and the buttons are both plastic with elastic deformability.

Furthermore, the fixing frame is provided with a snap hook at both sides of its left end.

The fixing device comprises a pull strip and snap strips connected to the pull strip at both sides of the pull strip, respectively, both of the snap strips being connected to the pull strip via the weakening portion. Each of the snap strips is provided with at least one barb-like buckle in cooperation with the snap hook, wherein the fixing frame and the fixing device are fixedly connected together by means of snap connection of the barb-like buckle and the snap hook.

After the needle guide holder has been used, the fixing device is pulled off from the position of the weakening portion by pulling the pull strip to separate the pull strip from the snap strips, thereby realizing a pull-off self-destructive design of the needle guide holder, so that the possibility of cross-infection caused by using the same needle guide holder by different patients can be avoided.

Preferably, the weakening portion is a row of discontinuous through holes or a groove.

The fixing frame is provided, therein, with one or more fixing bumps or fixing pits for fixing the ultrasonic probe.

The fixing bumps (or fixing pits) can cooperate with pits (or bumps) on the ultrasonic probe, so that the ultrasonic probe and the needle guide holder are fixed more firmly. The present invention has the following advantageous effects: the needle guide holder of the present invention is a disposable self-destructive needle guide holder, which makes use of the pull-off self-destructive design of the fixing device, wherein the needle guide holder can be detached from the ultrasonic probe only by destroying the fixing device by means of the weakening portion, thereby achieving the purpose of a single use of the needle guide holder, preventing a reuse of the needle guide holder, ensuring use sanitation of the needle guide holder better and avoiding the possibility of cross-infection caused by using the same needle guide holder by different patients. Besides, the needle guide holder of the present invention is a needle guide holder having high adaptability, which can achieve the purpose of the replacement of puncture needles of different sizes and specifications by replacing the sliding frame, puncture different sites, perform a number of treatments on the same patient just through the replacement of the sliding frame without replacing the fixing device and the fixing frame, save the treatment time, improve the puncture effect and save the cost. In addition, in a treatment process, the fixing frame can be separated from the sliding frame so as to realize a function that the puncture needle is left in the human body for a subsequent treatment, while the needle guide holder and the ultrasonic probe can be removed from the human body.

Meanwhile, the needle guide holder of the present invention, by holding the buttons, can conveniently and accurately adjust the needle insertion angle. The needle guide holder of the present invention does not have any threaded structure, and is convenient and efficient for installation and use.

In the FIGS., 1a: frame body; 11a: fixing frame; 111a: sliding groove; 112a: snap groove; 113a: through groove; 1131a: first boss; 114a: arc-shaped concave surface; 115a: accommodating groove; 12a: sliding frame; 121a: sliding portion; 1211a: protrusion; 1212a: puncture needle groove; 122a: snapping portion; 1221a: elastic snap lock; 12211a: projection; 2a: fixing device; 21a: pull strip; 211a: pull head; 22a: snap strip; 221a: barb-like buckle; 2211a: second boss; 23a: weakening portion; 1b: frame body; 11b: fixing frame; 111b: connecting portion; 1111b: rotation hole; 1112b: angle regulation hole A; 1113b: angle regulation hole B; 1114b: arc-shaped hole; 112b: hook; 113b: fixing bump; 12b: rotary needle frame assembly; 121b: rotary needle frame body; 1211b: guide groove; 1212b: concave snap point; 1213b: columnar protrusion; 1214b: angle regulation bump; 1215b: round hole; 122b: sliding frame; 1221b: puncture needle groove; 1222b: guide rail; 1223b: convex snap point; 2b: fixing device; 21b: pull strip; 211b: pull head; 22b: snap strip; 221b: barb-like buckle; 23b: weakening portion; 3b: button; 31b: snap groove; 32b: fixing head.

DETAILED DESCRIPTION

Hereinafter, the structures of the present invention will be explained in detail with reference to the figures.

As shown in FIGS. 1-11, a needle guide holder provided by a first embodiment of the present invention, which is used for fixing medical puncture needles and ultrasonic probes, comprises a frame body 1a and a fixing device 2a used in coordination with the frame body 1a, the fixing device 2a being mounted on the frame body 1a and provided with a weakening portion 23a. The frame body 1a and the fixing device 2a are both made of plastic materials harmless to the human body, and have low manufactory costs. The weakening portion 23a is formed through cutting or grinding by means of a cutting tool, or through melting by thermal deformation. In a preferred embodiment, the weakening portion 23a of the present patent may be composed of intermittently connected columnar structures, or a row of intermittent through holes, or a non-penetrating groove, which may be single-sided or double-sided, or saw-toothed connections resembling the edge of a stamp. The structure of the weakening portion 23a, which is not limited to the enumeration of the present invention, may be any structure producing a weakening function, and it is preferred to be produced via a single injection molding.

In the needle guide holder provided by the first embodiment of the present invention, the frame body 1a comprises a fixing frame 11a and a sliding frame 12a detachably mounted on the fixing frame 11a, and a puncture needle groove 1212a is opened on the sliding frame 12a. When there is a need to replace the puncture needle, it only requires to detach and replace the sliding frame 12a for the application of puncture needles with different diameters so as to check or treat different sites. In this case, there is no need to replace the entire needle guide holder, thereby saving the cost and replacement time of the needle guide holder. Meanwhile, in a treatment process, the fixing frame 11a can be separated from the sliding frame 12a so as to realize a function that the puncture needle is left in the human body for a subsequent treatment, but the needle guide holder and the ultrasonic probe can be removed from the human body.

In the needle guide holder provided by the first embodiment of the present invention, the sliding frame 12a is slidably connected to the fixing frame 11a. The sliding frame 12a has a sliding portion 121a and a snapping portion 122a, both sides of the sliding portion 121a are provided with protrusions 1211a, and the puncture needle groove 1212a is opened at the bottom of the sliding portion 121a: and both sides of the snapping portion 122a are provided with elastic snap locks 1221a, and each of the elastic snap locks 1221a has a projection 12211a. The fixing frame 11a is opened with sliding grooves 111a at sites thereon in coordination with the protrusions 1211a, and the fixing frame 11a is slidable in the sliding grooves 111a. The fixing frame 11a is provided with accommodating grooves 115a at sites thereon corresponding to the elastic snap locks 1221a, and the elastic snap locks 1221a are slidable in the accommodating grooves 115a, and the accommodating grooves 115a are provided with snap grooves 112a at sites therein corresponding to the projections 12211a, and the projections 12211a can be placed in the snap grooves 112a. The elastic snap locks 1221a are made of a non-metallic material, and, particularly, make use of the elastic deformability of a material such as plastics to realize locking and fixing. Such a setting mode is simple and practical. The snap groove 112a, which is also not limited to the groove body in a specific implementation process, may also be a recess and any concave structure capable of cooperation with the projection 12211a.

In the needle guide holder provided by the first embodiment of the present invention, both sides of the fixing frame 11a are provided with through grooves 113a (the through grooves 113a are opened on the fixing frame 11a and located directly below the snapping portion 122a of the sliding frame 12a), both of which have first bosses 1131a. The fixing device 2a comprises a pull strip 21a and snap strips 22a connected to both sides of one end of the pull strip 21a, respectively, and the two snap strips 22a are both connected to the pull strip 21a through the weakening portion 23a. Each of the snap strips 22a is provided with at least one barb-like buckle 221a in coordination with the through groove 113a, and the barb-like buckle 221a is provided with second bosses 2211a at sites thereon corresponding to the first bosses 1131a, wherein the frame body 1a and the fixing device 2a are fixedly connected by snapping of the first bosses 1131a and the second bosses 2211a. There may be one barb-like buckle 221a or several barb-like buckles 221a arranged in a straight line. After the barb-like buckle 221a of the fixing device 2a is engaged with the first boss 1131a of the through groove 113a, it cannot be detached manually.

The specific method for the usage of the needle guide holder provided by the first embodiment of the present invention is as follows: the sliding portion 121a of the sliding frame 12a is inserted into the sliding groove 111a of the fixing frame 11a, and the projection 12211a of the sliding frame 12a is embedded in the snap groove 112a of the fixing frame 11a, so as to keep the fixing frame 11a and the sliding frame 12a fixed. The inner wall of an arc-shaped concave surface 114a of the fixing frame 11a wraps the outer contour of the ultrasonic probe, the barb-like buckle 221a of the fixing device 2a is inserted into the through groove 113a of the fixing frame 11a to wrap the fixing frame 11a and the ultrasonic probe, and the second boss 2211a of the barb-like buckle 221a coordinates with the first boss 1131a in the through groove 113a so as to fix the fixing frame 11a and the ultrasonic probe. The fixing frame 11a and the fixing device 2a, together, relatively lock and wrap the outer contour of the ultrasonic probe. At this time the needle guide holder has been installed, the ultrasonic probe and the needle guide holder are then put into the body, different puncture needles are selected according to different diseases and sites, and the puncture needle is inserted into the puncture needle groove 1212a; next, the sliding frame 12a and the fixing frame 11a are separated, the sliding frame 12a is first taken out of the body and the puncture needle is kept still, the fixing frame 11a, at this time, is still fixed on the ultrasonic probe, and the fixing frame 11a is then removed from the body together with the ultrasonic probe. The puncture needle remains in the body to realize the treatment operation, and after the treatment is completed, the puncture needle is pulled out. At this time, the fixing frame 11a and the fixing device 2a are locked with the ultrasonic probe. After the first boss 1131a disposed in the through groove 113a is engaged with the second boss 2211a of the barb-like buckle 221a, they cannot be separated. Thus, the user can only destroy the weakening portion 23a by pulling the pull strip 21a (the weakening portion 23a is first torn due to less stress), and finally finishes the removal of the fixing frame 11a and the fixing device 2a from the ultrasonic probe, so as to avoid a reuse.

Figure 1:
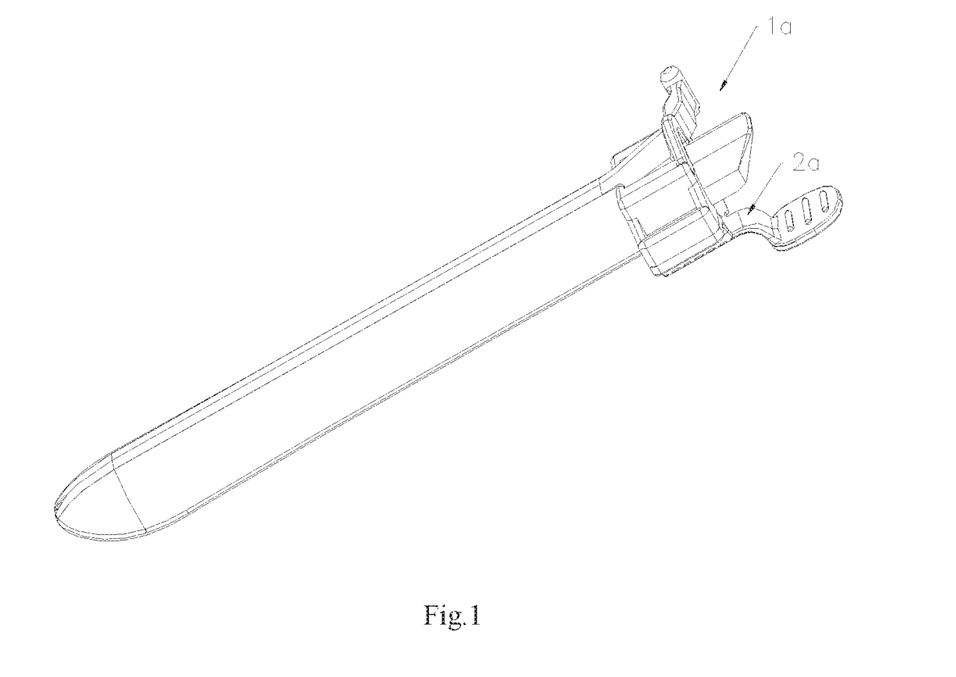
FIG. 1 is a front structure schematic diagram of a needle guide holder according to a first embodiment of the present invention.
Figure 2:
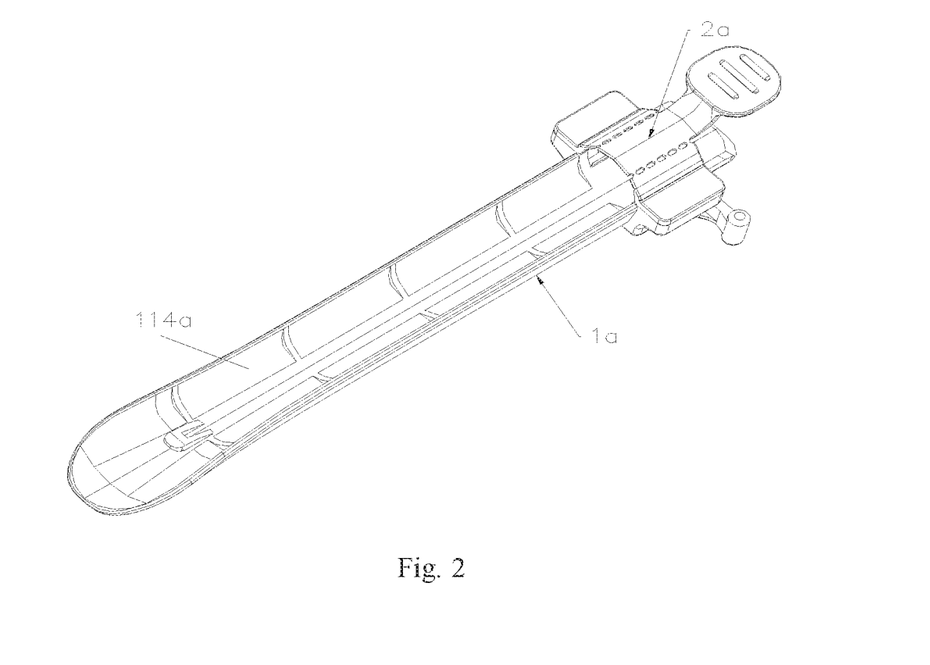
FIG. 2 is a back structure schematic diagram of the needle guide holder according to the first embodiment of the present invention.
Figure 3:
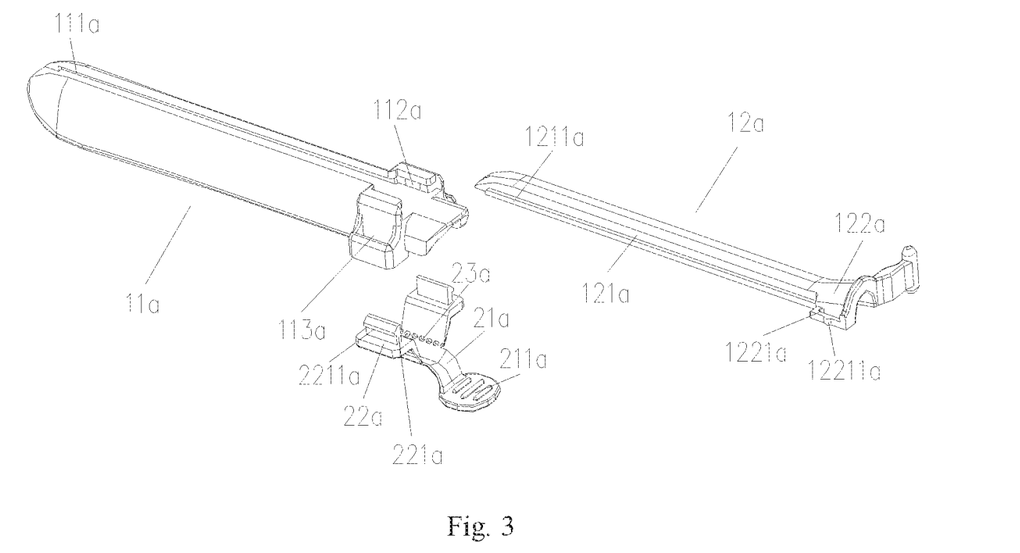
FIG. 3 is an exploded view of the needle guide holder according to the first embodiment of the present invention.
Figure 4:
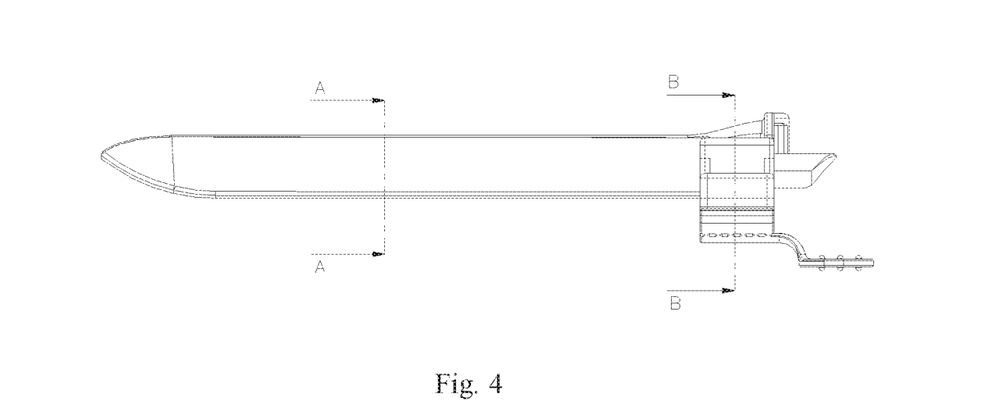
FIG. 4 is a front view of the needle guide holder according to the first embodiment of the present invention.
Figure 5:
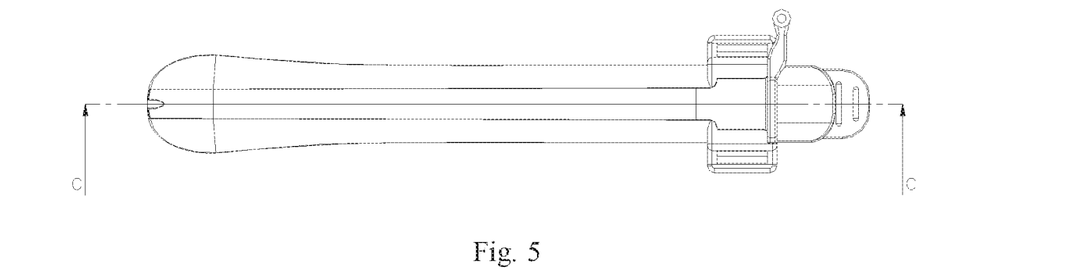
FIG. 5 is a top view of the needle guide holder according to the first embodiment of the present invention.
Figure 6:
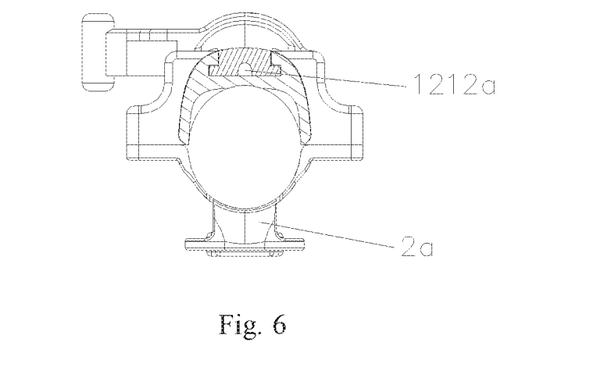
FIG. 6 is an A-A sectional view of FIG. 4.
Figure 7:
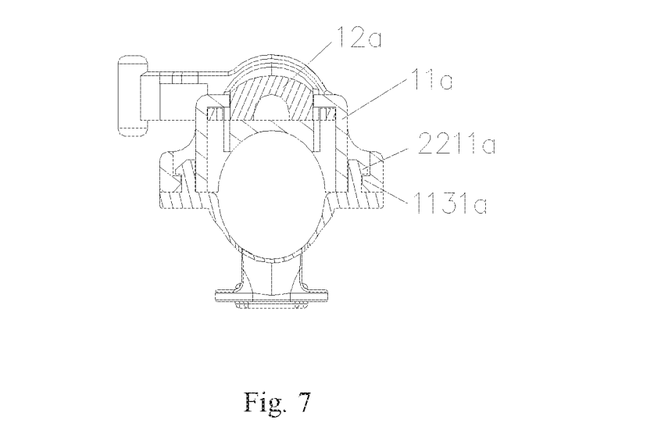
FIG. 7 is a B-B sectional view of FIG. 4.
Figure 8:
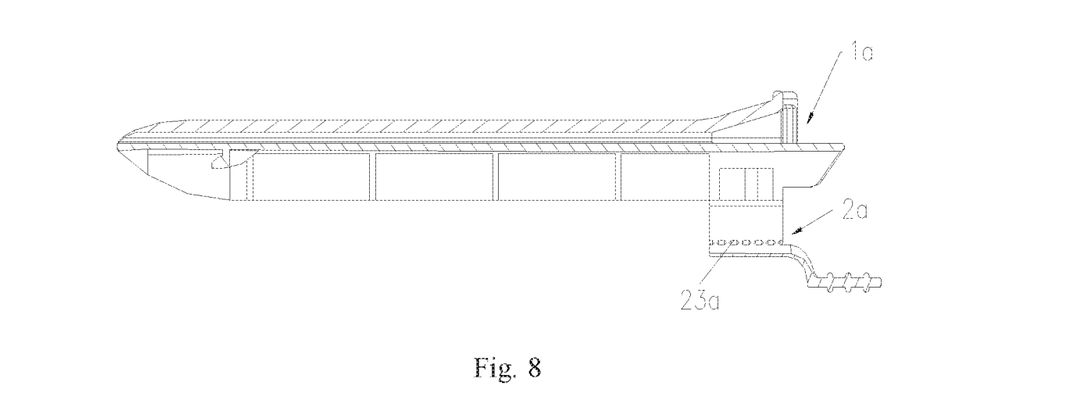
FIG. 8 is a C-C sectional view of FIG. 5.
Figure 9:
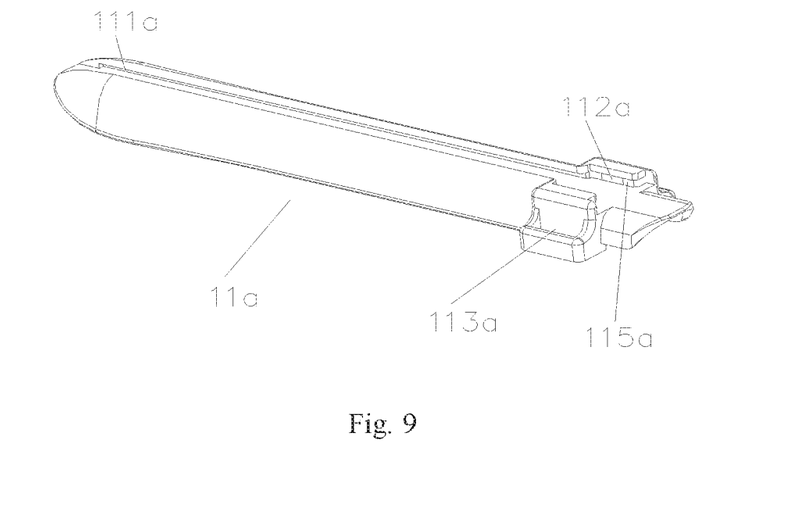
FIG. 9 is a structure schematic diagram of a fixing frame according to the first embodiment of the present invention.
Figure 10:
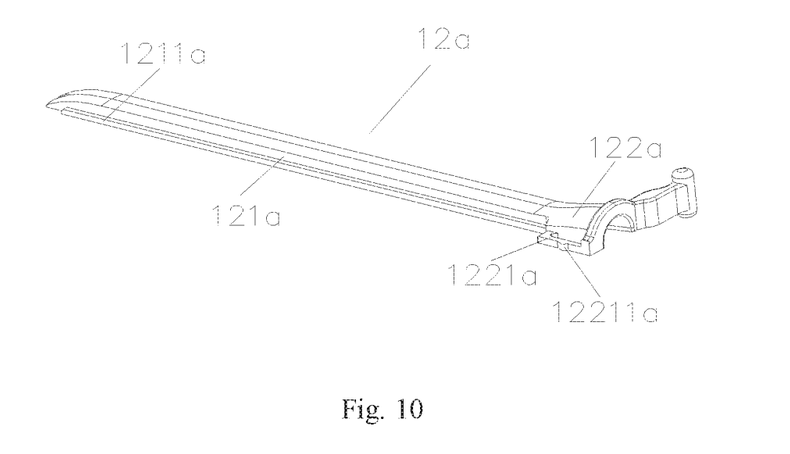
FIG. 10 is a structure schematic diagram of a sliding frame according to the first embodiment of the present invention.
Figure 11:
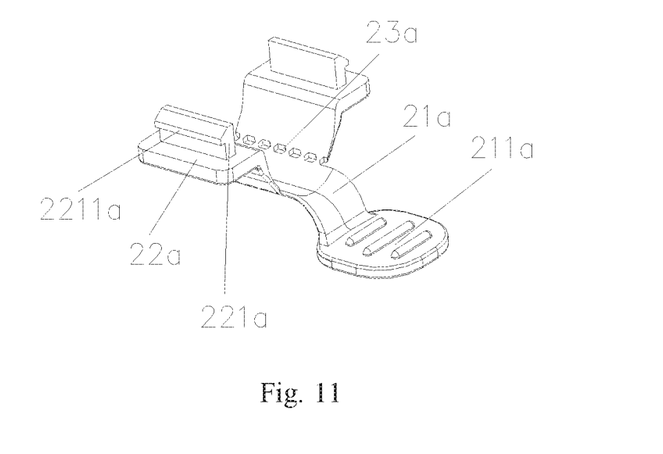
FIG. 11 is a structure schematic diagram of a fixing device according to the first embodiment of the present invention.

Moreover, the insertion of different barb-like buckles 221a on the snap strips 22a into the through grooves 113a, for the cooperation of the second bosses 2211a with the first bosses 1131a, can meet the requirement of fixing ultrasonic probes with different outer diameters. If the number of the barb-like buckle 221a on the snap strip 22a is one, the requirement of fixing an ultrasonic probe with a different outer diameter can be met only by the replacement with a fixing device 2a different in specification and size and without additionally equipping a different fixing frame 11a, thereby increasing the versatility of the fixing frame 11a and helping to reduce the use cost. If there are several barb-like buckles 221a arranged in a straight line on the snap strips 22a, the snap strips 22a per se have the ability to adapt to ultrasonic probes with different outer diameters. The ultrasonic probes with different outer diameters can be fixed by engaging the second bosses 2211a of different barb-like buckles 221a with the first bosses 1131a in the through grooves 113a.

After the use, the pull strip 21a can be pulled through a pull head 211a, so that the pull strip 21a and the snap strip 22a are pulled off at the joint thereof (the weakening portion 23a) and the fixing device 2a fails. That is, the fixing frame 11a and the ultrasonic probe can be separated, and the entire needle guide holder can be discarded at the same time (the fixing frame 11a, the sliding frame 12a and the puncture needle need to be discarded at the same time to avoid a reuse of the entire needle guide holder), for the convenience of the separation of the pull strip 21a and the snap strip 22a. The disposable self-destructive needle guide holder can be detached from the ultrasonic probe only by a pull-off self-destructive design on the fixing device 2a, thereby accomplishing the purpose of a single use of the needle guide holder, preventing a reuse of the needle guide holder, ensuring use sanitation of the needle guide holder better and avoiding the possibility of cross-infection caused by using the same needle guide holder by different patients.

Figure 12:
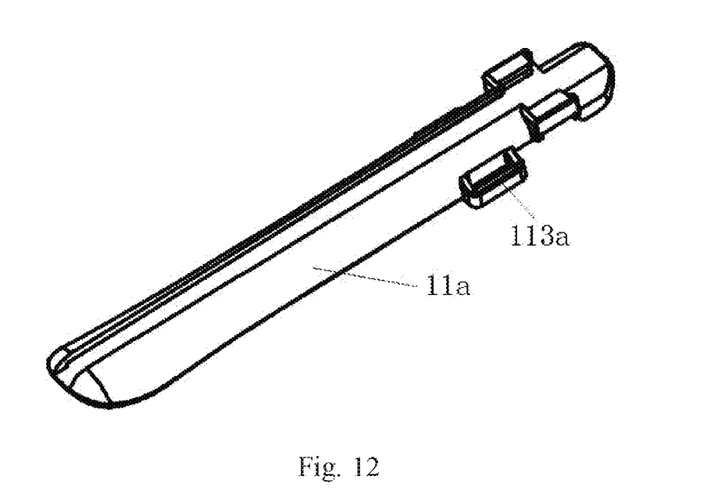
FIG. 12 is a structure schematic diagram of a fixing frame according to a second embodiment of the present invention.
Figure 13:
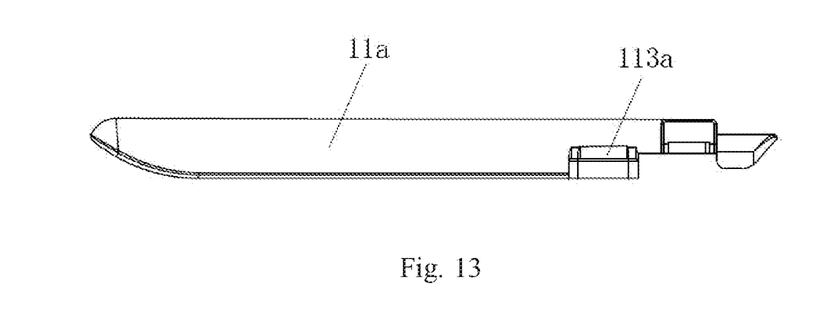
FIG. 13 is a front view of the fixing frame according to the second embodiment of the present invention.
Figure 14:
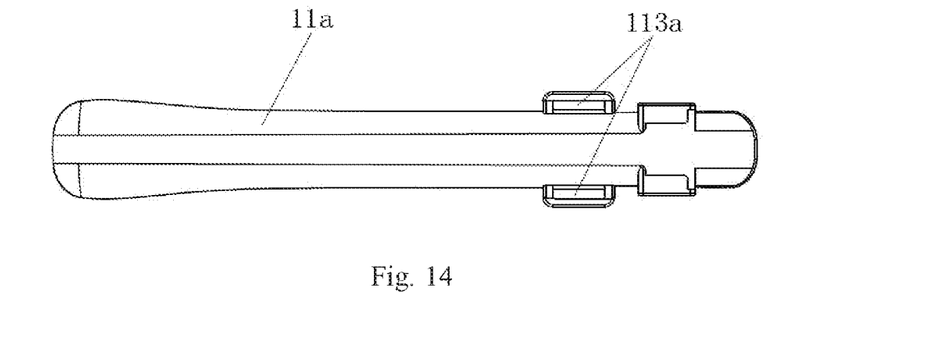
FIG. 14 is a top view of the fixing frame according to the second embodiment of the present invention.

As shown in FIGS. 12-14, a needle guide holder provided by a second embodiment of the present invention is different from the needle guide holder provided by the first embodiment in the structure of the fixing frame 11a. The specific difference lies in the site on the fixing frame 11a for installing the through groove 113a of the fixing device 2a, wherein the through groove 113a of the first embodiment is opened on the fixing frame 11a and located directly below the snapping portion 122a of the sliding frame 12a, whereas the through groove 113a of the second embodiment is opened on the fixing frame 11a and located below the sliding portion 121a of the sliding frame 12a. Besides, the shape of the right end of the fixing frame 11a of the needle guide holder provided by the second embodiment is also slightly different from that of the fixing frame 11a of the needle guide holder of the first embodiment.

As shown in FIGS. 15-19, a needle guide holder provided by a third embodiment of the present invention, which is used for fixing medical puncture needles and ultrasonic probes, comprises a frame body 1b and a fixing device 2b used in coordination with the frame body 1b, the fixing device 2b being mounted on the frame body 1b and provided with a weakening portion 23b. The frame body 1b and the fixing device 2b are both made of plastic materials harmless to the human body, and have low processing costs. The weakening portion 23b is formed through cutting or grinding by means of a cutting tool, or through melting by thermal deformation. In a preferred solution, the weakening portion 23b of the present patent may be composed of intermittently connected columnar structures, or a row of intermittent through holes, or a non-penetrating groove, which may be single-sided or double-sided, or saw-toothed connections resembling the edge of a stamp. The structure of the weakening portion 23b, which is not limited to the enumeration of the present invention, may be any structure producing a weakening function, and it is preferred to be produced via a single injection molding.

In the needle guide holder provided by the third embodiment of the present invention, the frame body 1b comprises a fixing frame 11b and a rotary needle frame assembly 12b.

In the needle guide holder provided by the third embodiment of the present invention, the fixing frame 11b is further provided, therein, with one or more fixing bumps 113b or fixing pits (the fixing bump 113b is only one specific fixing manner, and different ultrasonic probes may have different pits or bumps at different sites, so different fixing bumps 113b or fixing pits may be disposed on the fixing frame 11b for cooperation with the ultrasonic probe) for fixing the ultrasonic probe, and the needle guide holder is a plastic needle guide holder capable of cooperation and fixation with the pits or bumps on the ultrasonic probe.

Figure 20:
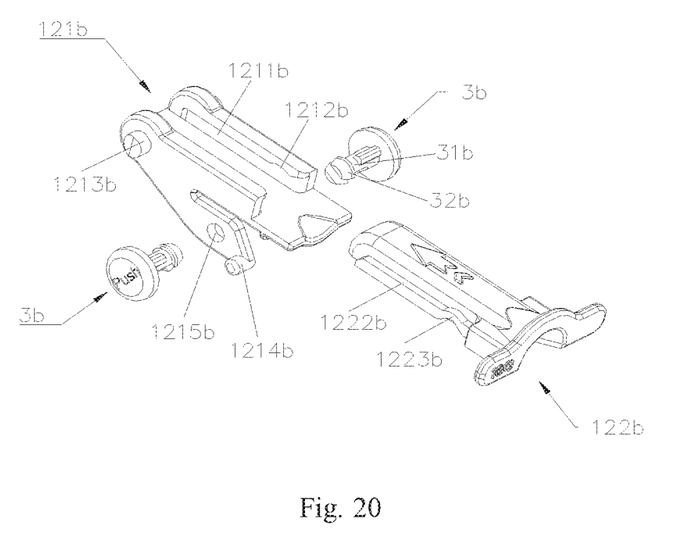
FIG. 20 is an exploded view of a rotary needle frame assembly according to the third embodiment of the present invention.
Figure 21:
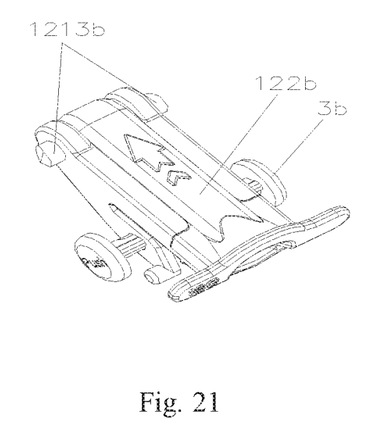
FIG. 21 is an assembly structure schematic diagram of the rotary needle frame assembly according to the third embodiment of the present invention.
Figure 22:
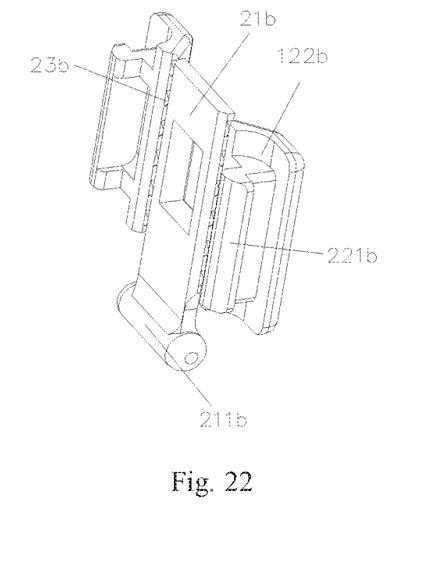
FIG. 22 is a structure schematic diagram of a fixing device according to the third embodiment of the present invention.
Figure 23:
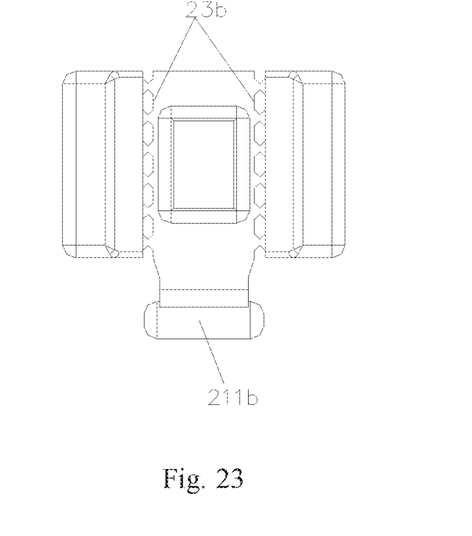
FIG. 23 is a rear view of the fixing device according to the third embodiment of the present invention.
Figure 24:
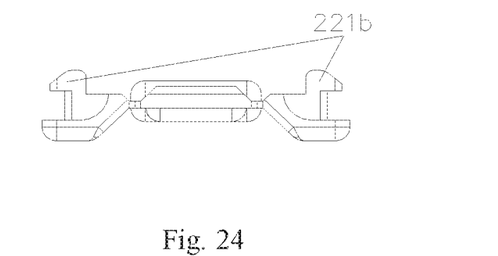
FIG. 24 is a top view of the fixing device according to the third embodiment of the present invention.
Figure 25:
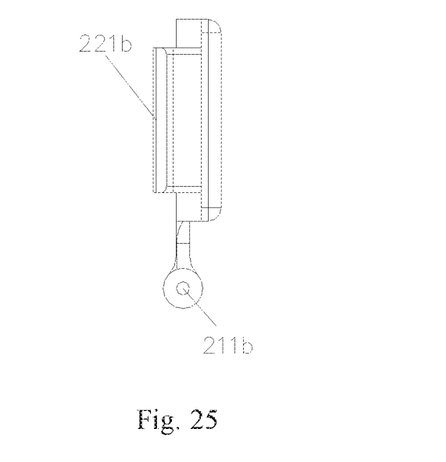
FIG. 25 is a side view of the fixing device according to the third embodiment of the present invention.

As shown in FIGS. 20-21, in the needle guide holder provided by the third embodiment of the present invention, the rotary needle frame assembly 12b comprises a rotary needle frame body 121b and a sliding frame 122b detachably mounted on the rotary needle frame body 121b, wherein a puncture needle groove 1221b is opened on the sliding frame 122b. The rotary needle frame body 121b is slidably connected to the sliding frame 122b. Both sides of the sliding frame 122b are provided with guide rails 1222b, and the guide rails 1222b are both provided with convex snap points 1223b.

The rotary needle frame body 121b is provided with guide grooves 1211b at sites thereon corresponding to the guide rails 1222b, and the guide grooves 1211b are provided with concave snap points 1212b at sites thereon corresponding to the convex snap points 1223b, wherein
the convex snap points 1223b can be placed in the concave snap points 1212b, and the guide rails 1222b are slidable in the guide grooves 1211b.

The sliding frame 122b is provided with guide rails 1222b and convex snap points 1223b, so that the guide rails 1222b can be slid into the guide grooves 1211b disposed on the rotary needle frame body 121b, and the sliding frame 122b is fixed by the cooperation of the convex snap points 1223b and the concave snap points 1212b on the rotary needle frame body 121b. The rotary needle frame body 121b has an elastic deformability, so that, through an elastic deformation characteristic of the concave snap points 1212b, the sliding frame 122b can be detached at any time during the operation to realize the overall separation of the sliding frame 122b and the rotary needle frame body 121b (the sliding frame 122b and the rotary needle frame body 121b are both made of non-metallic materials, in particular materials having an elastic deformability such as plastics, so as to realize locking and fixing of the sliding frame 122b and the rotary needle frame body 121b by the cooperation of the convex snap points 1223b and the concave snap points 1212b; such a setting mode is simple and practical), for the application of puncture needles with different diameters so as to check or treat different sites. In this case, there is no need to replace the entire needle guide holder, thereby saving the cost and replacement time of the needle guide holder. Meanwhile, in a treatment process, the sliding frame 122b can be separated from the rotary needle frame body 121b so as to realize a function that the puncture needle is left in the human body for a subsequent treatment, but the needle guide holder and the ultrasonic probe can be removed from the human body.

Figure 15:
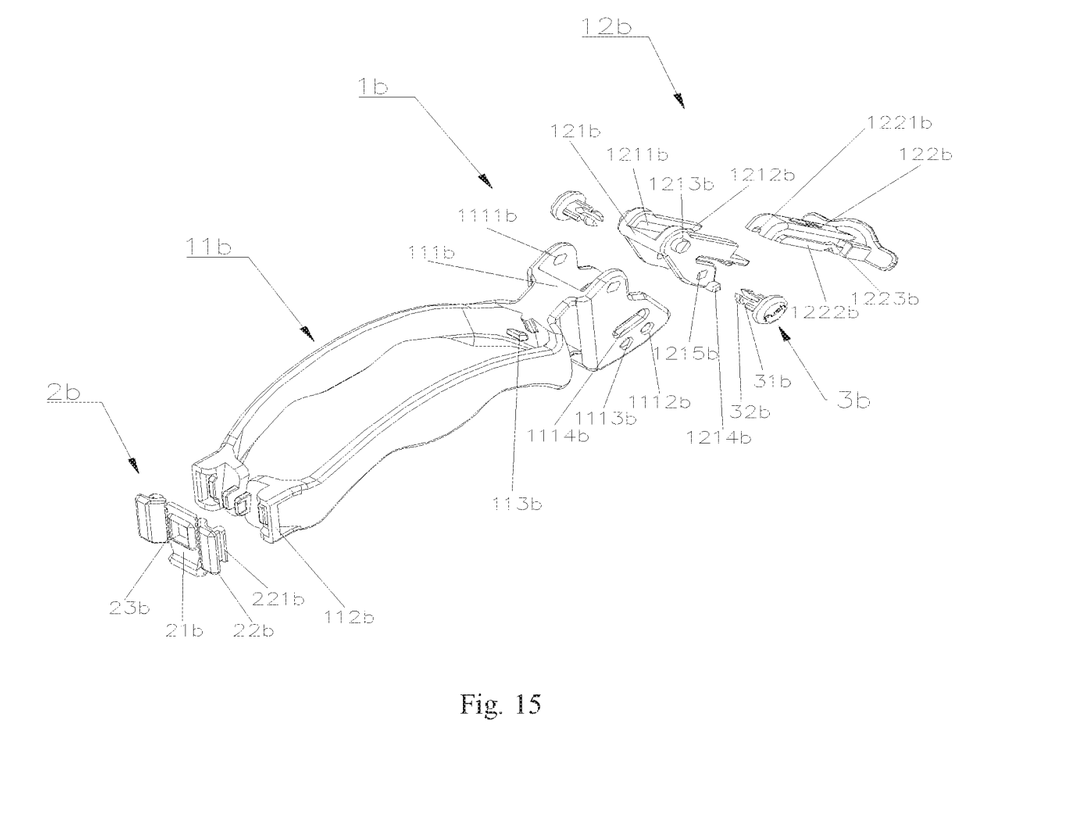
FIG. 15 is an exploded view of a needle guide holder according to a third embodiment of the present invention.
Figure 16:
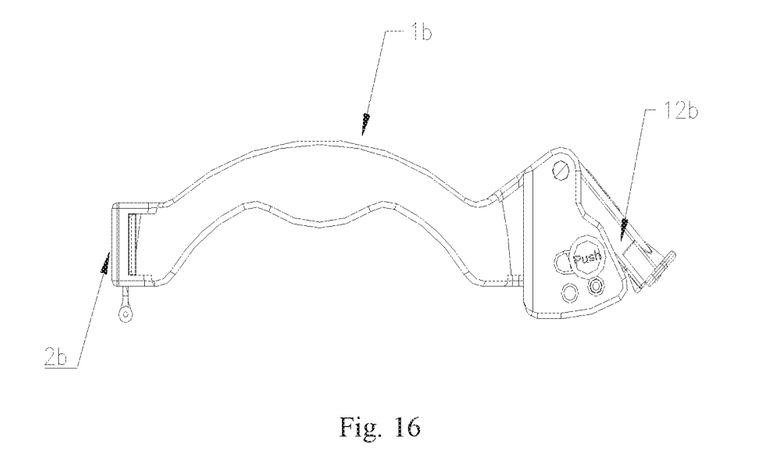
FIG. 16 is a front view of the needle guide holder according to the third embodiment of the present invention.
Figure 17:
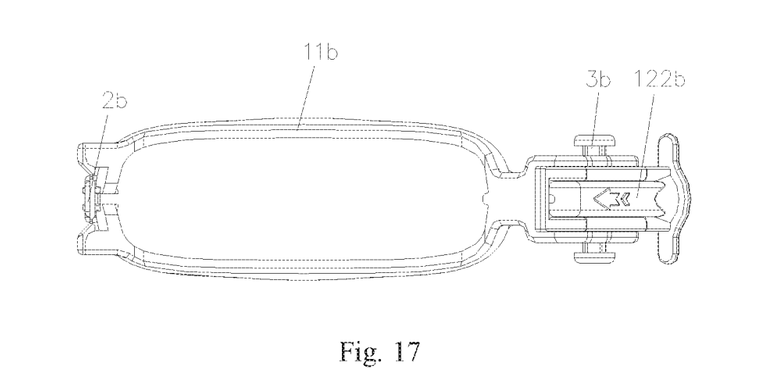
FIG. 17 is a top view of the needle guide holder according o the third embodiment of the present invention.
Figure 18:
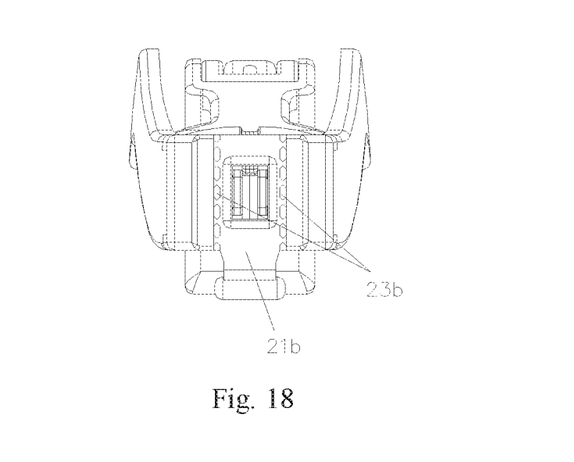
FIG. 18 is a left view of the needle guide holder according to the third embodiment of the present invention.
Figure 19:
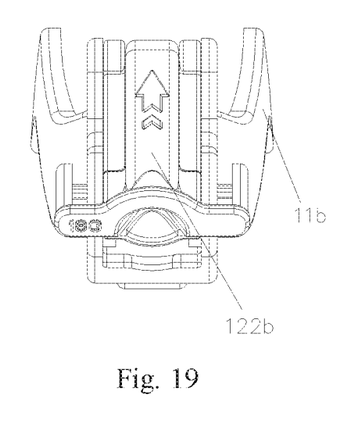
FIG. 19 is a right view of the needle guide holder according to the third embodiment of the present invention.

As shown in FIG. 15, in the needle guide holder provided by the third embodiment of the present invention, the fixing frame 11b has a connecting portion 111b at its right end, a pair of rotation holes 1111b, two pairs of angle regulation holes 1112b, 1113b (one pair is angle regulation holes A1112b and the other pair is angle regulation holes B1113b) and a pair of arc-shaped holes 1114b are opened on the connecting portion 111b, the angle regulation holes 1112b, 1113b and the arc-shaped holes 1114b are all located on arcs of circles formed with the rotation holes 1111b as centers, and a plane where the circles lie is perpendicular to a straight line where the pair of rotation holes 1111b are located.

The rotary needle frame body 121b is provided with columnar protrusions 1213b at sites thereon corresponding to the rotation holes 1111b, angle regulation bumps 1214b at sites thereon corresponding to the angle regulation holes 1112b, 1113b, and round holes 1215b at sites thereon corresponding to the arc-shaped holes 1114b, wherein
the columnar protrusions 1213b can all be placed in the rotation holes 1111b; the angle regulation bumps 1214b can be placed in the angle regulation holes 1112b, 1113b; and the rotary needle frame assembly 12b is further provided with two buttons 3b, and the buttons 3b are both opened, in the middle thereof, with snap grooves 31b, both of which are placed in the arc-shaped holes 1114b and the round holes 1215b.

The materials of the frame body 1b and the button 3b are both plastics with an elastic deformability.

In the needle guide holder provided by the third embodiment of the present invention, the fixing frame 11b has an elastic deformation characteristic, and the rotation holes 1111b on the fixing frame 11b are deformed to both sides, so that the two columnar protrusions 1213b on the rotary needle frame body 121b are inserted into the rotation holes 1111b in the fixing frame 11b, The rotary needle frame body 121b, then through its own elastic deformation characteristic, can make the angle regulation bumps 1214b buckled into the angle regulation holes A1112b or angle regulation holes B1113b in the fixing frame 11b. The buttons 3b have fixing heads 32b, on which U-shaped grooves are opened. The buttons 3b are deformed through the fixing heads 32b thereon, pass through the arc-shaped holes 1114b on the fixing frame 11b, and are then inserted into the round holes 1215b on the rotary needle frame body 121b for fixation (i.e., placing the snap grooves 31b of the buttons 3b in the arc-shaped holes 1114b and the round holes 1215b). By pressing two knobs, the two angle regulation bumps 1214b on the rotary needle frame body 121b, after inward deformation, can be enabled to fall into the angle regulation holes A1112b or angle regulation holes B1113b on the fixing frame 11b, to accomplish the purpose of selecting an angle for insertion of the needle so as to make the operation convenient and accurate.

As shown in FIGS. 22-25, in the needle guide holder provided by the third embodiment of the present invention, the fixing frame 11b is provided with hooks 112b on both sides of a left end thereof. The fixing device 2b comprises a pull strip 21b and snap strips 22b connected to both sides of the pull strip 21b, respectively, and the two snap strips 22b are both connected to the pull strip 21b through the weakening portion 23b. Each of the snap strips 22b is provided with at least one barb-like buckle 221b in coordination with the hook 112b, wherein the fixing frame 11b and the fixing device 2b are fixedly connected by snapping of the barb-like buckle 221b and the hook 112b. On each of the snap strips 22b, there may be one barb-like buckle 221b or several barb-like buckles 221b arranged in a straight line. After the barb-like buckle 221b of the fixing device 2b is engaged with the hook 112b, it cannot be detached manually.

At the time of using the needle guide holder provided by the third embodiment of the present invention, the type-B ultrasonic probe is first wrapped with a probe cover (the ultrasonic probe of the present invention may be a type-B ultrasonic probe or other ultrasonic probes, which is determined according to actual medical needs), the needle guide holder is then installed to make the fixing bumps 113b on the fixing frame 11b aligned with and close to corresponding pit sites on the type-B ultrasonic probe, and after the frame body 1b is installed in place, the barb-like buckles 221b of the snap strips 22b are buckled into the hooks 112b in the frame body 1b. After the puncture operation is completed, the pull head 211b on the pull strip 21b is manually pulled, so that the weakening portion 23b between the pull strip 21b and the snap strip 22b is destroyed (the weakening portion 23b is first torn due to less stress), and the needle guide holder is thus completely destroyed and removed.

The above are only preferred embodiments of the present invention and are not intended to limit the present invention. Any modifications, equivalent substitutions, simple improvements and the like made in the essential contents of the present invention shall be included in the scope of protection of the present invention.

The invention claimed is:

1. A needle guide holder for fixing a medical puncture needle and an ultrasonic probe, comprising: a holder body and a fixing device used in cooperation with the holder body, the fixing device being mounted onto the holder body and provided with a weakening portion, wherein the holder body includes a fixing frame and a rotary needle holder assembly, the fixing frame being rotatably connected to the rotary needle holder assembly, wherein the rotary needle holder assembly includes a rotary needle holder body and a sliding frame detachably mounted to the rotary needle holder body, wherein the fixing frame has a connecting portion at its right end, the connecting portion being provided with a pair of rotation holes, two pairs of angle adjusting holes and a pair of arc-shaped holes therein, and wherein the rotary needle holder body is provided with a columnar protrusion at each location thereon that corresponds to the rotation holes, with an angle adjusting bump at each location thereon that corresponds to the angle adjusting holes, and with a circular hole at each location thereon that corresponds to the arc-shaped holes, and wherein the sliding frame is provided with a puncture needle groove thereon.

2. The needle guide holder according to claim 1, wherein both sides of the sliding frame are each provided with a guide rail, each guide rail being provided with a snap bump.

3. The needle guide holder according to claim 2, wherein the rotary needle holder body is provided with a guide groove at each location thereon that corresponds to the guide rail, the guide groove being provided with a snap pit at each location thereon that corresponds to the snap bump, wherein the snap bump can be placed in the snap pit, and the guide rail is slidable in the guide groove.

4. The needle guide holder according to claim 1, wherein the angle adjusting holes and the arc-shaped holes are all located on arcs of circles formed with the rotation holes being centers of the circles, and a plane where the circles lie is perpendicular to a straight line where the pair of rotation holes are located.

5. The needle guide holder according to claim 4, wherein the columnar protrusions can be placed in the rotation holes;

the angle adjusting bumps can be placed in the angle adjusting holes; and the rotary needle holder assembly is further provided with two buttons, the buttons each being provided, in the middle thereof, with a snap groove, each snap groove being placed in the arc-shaped holes and the circular holes.

6. The needle guide holder according to claim 1, wherein the fixing frame is provided with a snap hook at both sides of its left end.

7. The needle guide holder according to claim 6, wherein the fixing device includes a pull strip and snap strips connected to the pull strip at both sides of the pull strip, respectively, both of the snap strips each being connected to the pull strip via the weakening portion.

8. The needle guide holder according to claim 7, wherein each snap strip is provided with at least one barb-like buckle in cooperation with the snap hook, and wherein the fixing frame and the fixing device are fixedly connected together by means of snap connection of the barb-like buckle and the snap hook.

9. The needle guide holder according to claim 1, wherein the fixing frame is provided, therein, with one or more fixing bumps or fixing pits for fixing the ultrasonic probe.

10. The needle guide holder according to claim 1, wherein the weakening portion is a row of discontinuous through holes or a groove.

* * * * *